United States Patent [19]

Holzner

[11] 4,217,250

[45] Aug. 12, 1980

[54] PROCESS FOR THE STABILIZATION OF PERFUMES

[75] Inventor: Günter Holzner, Grand-Lancy, Switzerland

[73] Assignee: Firmenich SA, Geneva, Switzerland

[21] Appl. No.: 906,659

[22] Filed: May 16, 1978

[30] Foreign Application Priority Data

May 24, 1977 [CH] Switzerland .......................... 6377/77

[51] Int. Cl.$^2$ ................................................ C11B 9/00
[52] U.S. Cl. ............................ 252/522 R; 252/522 A; 252/DIG. 17; 252/174; 252/108; 424/65; 424/70; 424/76; 424/358; 252/89.1
[58] Field of Search .......................... 252/522, DIG. 17

[56] References Cited

U.S. PATENT DOCUMENTS

| | | | |
|---|---|---|---|
| 3,567,119 | 3/1971 | Wilbert | 252/522 |
| 3,954,963 | 5/1976 | Kuderna | 252/522 |
| 3,954,964 | 5/1976 | Kuderna | 252/522 |

FOREIGN PATENT DOCUMENTS

2011893  3/1970  France ..................................... 252/522

*Primary Examiner*—Veronica O'Keefe
*Attorney, Agent, or Firm*—Pennie & Edmonds

[57] ABSTRACT

Perfumes in general are stabilized, particularly against the coloration produced by the presence of heavy metals by the addition of liposoluble heavy metals complexing agents.

5 Claims, No Drawings

PROCESS FOR THE STABILIZATION OF PERFUMES

THE INVENTION

The present invention relates to a method for stabilizing perfumes, perfume bases and perfuming ingredients which consist in the addition thereto of a liposoluble heavy metals complexing agent.

The invention relates further to a perfume, a perfume base or a perfuming ingredient which contains a liposoluble heavy metals complexing agent.

BACKGROUND OF THE INVENTION

Denaturation and deterioration of both raw materials and end-products in general are matters of increasing concern to the perfume industry. Denaturation often consists in the excessive coloration which gradually appears during the storage or the manufacture of perfumes, this effect being accompanied by a modification of their odorous characters. The extent of this phenomenon depends on the nature of the raw materials utilized for the perfumes manufacture, irrespective of whether they are of natural or synthetic origin, of the conditions of compounding and storage, and of course of the nature of the article to be perfumed, whether a soap, a detergent powder, a household material or a cosmetic product for instance. Normally, coloration results from the action exerted on perfumes by light, oxidation or excessive acidity or basicity. If certain of these factors are normally easy to correct, some others, like oxidation, represent major industrial problems whose solution is nowdays far from being satisfactory.

The solution which consists in employing anti-oxidizing agents such as p-t-butyl-hydroxy-toluene, p-t-butyl-hydroxy-anisole, ascorbic acid or tin dichloride is not fully adequate in all those cases where prolonged storage is required and where trace amounts of heavy metals are present, especially if activated by the action of light. Traces of heavy metals, namely iron and copper, often contaminate perfumery raw materials. They can be inactivated or even eliminated by treating them with citric, oxalic, phosphoric or tartaric acid, with tetracetic ethylenediamine or with certain of their salts. Sodium oxalate for instance is currently utilized for the preliminary treatment of low grade patchouli oil.

The major disadvantage of the above cited agents consists in the fact that they are all essentially insoluble in the current perfume media and they must consequently be used in large excess and eliminated from the treated medium. Their action is therefore temporary. A batch of patchouli oil treated with sodium oxalate, for instance, may be contaminated by heavy metals later on during following handling in the course of the manufacture of a perfumed finished product.

We have now discovered that these disadvantages can be overcome by utilizing liposoluble heavy metals complexing agents; consequently, the present invention provides a method for stabilizing perfumes, perfume bases and perfuming ingredients which consist in the addition thereto of a liposoluble heavy metals complexing agent.

PREFERRED EMBODIMENTS OF THE INVENTION

The term "perfume", as used throughout the present specification, is deemed to include indifferently mixtures of synthetic chemicals, essential oils or combinations of both synthetic chemicals and essential oils and solvents, supports or excipients. The terms "perfuming ingredients" is construed to define natural and artificial essential oils as well as synthetic chemicals. By the method of the invention it is now possible to stabilize perfumes, perfume bases and perfuming ingredients in a particularly effective and lasting fashion, independently of the manufacture, treatments or storage conditions which the said materials may be subjected to; coloration and odour denaturation can therefore be completely suppressed.

Useful liposoluble complexing agents in accordance with the invention include copolymers of ethylene and propylene oxide with ethylene-diamine. Such products belong to the class of compounds possessing the following chemical structure.

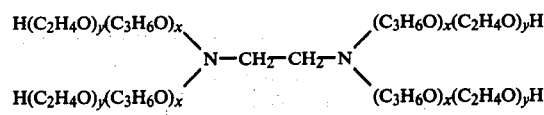

wherein symbols x and y each represents an integer greater than zero of identical or different value.

These compounds are non-ionic tensio-active materials used in the industry at present as emulsifiers, anti-foaming and antistatic agents.

Another class of useful liposoluble complexing agents in accordance with the invention comprises derivatives of phosphonic or diphosphonic acid, more particularly they include the esters derived from phosphoric or phosphonic acid and an ethoxylated fatty alcohol. These esters belong to the class of compounds of formula

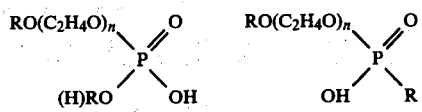

wherein n defines an integer greater than zero and symbol R an aliphatic radical preferably containing from 10 to 20 carbon atoms. These esters are also known in the chemical industry as non-ionic or anionic tensio-active materials usually utilized as detergents, emulsifiers, or anti-foaming and anti-static agents.

The above mentioned compounds are available in liquid, pasty or solid form; they are soluble in all the perfume media we have investigated and perfectly odour compatible with all the perfuming ingredients studied.

According to a preferred embodiment of the invention, the liposoluble complexing agents cited above can be used in combination with reagents able to neutralize the natural acidity of certain perfumes, such as for example triethanolamine.

In order to achieve the desired stabilizing effects, the liposoluble complexing agents of the invention can be used in proportions which can vary within a wide range depending on the nature of the perfumes or perfuming ingredients to which they are added and on the extent of their contamination by heavy metals. Typically, they can be utilized at concentrations varying from about 0.5 to 25% by weight based on the total weight of the finished perfume or perfume ingredient.

The above cited liposoluble complexing agents are materials easily available on the market in practically unlimited quantities.

Hereinbelow, we will mention in an exemplificatory way some of the derivatives which can be used in accordance with the invention. In addition to the therein indicated compounds, liposoluble derivatives of citric, tartaric and oxalic acid, more particularly alkylated or polyethoxylated derivatives thereof, can satisfactorily be used. In practice, any liposoluble compound able to complex heavy metals, such as iron and copper, can advantageously be used.

| Complexing agent | Characterization | Commercial Source[1] |
| --- | --- | --- |
| TETRONIC 701 | Copolymer of ethylene and propylene oxide with ethylene diamine | BASF Wyandotte |
| TETRONIC 1301 | Copolymer of ethylene and propylene oxide with ethylene diamine | BASF Wyandotte |
| HOSTAPHAT KL-340 | Ester of phosphoric acid with ethoxylated lauril alcohol | HOECHST AG |
| STRODEX MO-100 | Ethyl-hexyl-polyphosphate | DEXTER Chem. Corp. |
| KLEARFAC AB-270 | Acidic ester of phosphoric acid | BASF Wyandotte |
| MONAFAX L-10 | Ester of phosphoric acid | MONA Industries Inc. |
| MONAFAX 785 | Ester of phosphoric acid | MONA Industries Inc. |
| STEINAPHAT EAK 8190 | Ester of phosphoric acid and a polyethoxylated fatty alcohol | CHEMISCHE FABRIK GmbH |
| VARIFOS 2039 | Acidic ester of phosphoric acid | ASHLAND CHEM. |

[1]see Mc Cutcheon's, Detergents and Emulsifiers North American Edition (1975)

The invention is better illustrated by the following examples.

EXAMPLE 1

A certain quantity of patchouli oil has been divided in several portions of equal volume. To each one of them there was then added in a 1% by weight porportion one of the following compounds:
MONAFAX 785, MONAFAX L-10, KLEARFAC AB-270, VARIFOS 2039 (samples 1 to 4)

These samples, as well as an untreated sample of patchouli oil, were then stored in a stoppered glass vial and exposed to light during 4 weeks. After this period we could observe that the untreated sample was strongly colored (dark-brown) whereas samples 1 to 4 appeared slightly brown, in much the same way as the original patchouli oil. The above described operation was repeated by dissolving however each fraction in 95% ethanol at a concentration of 2% by weight. After 4-week exposure to light the untreated sample became brown, whereas samples 1 to 4 remained pale yellow, the colour of origin. From the point of view of their respective odour, samples 1 to 4 possessed a scent identical in all respects to that of original patchouli oil, whereas the brown sample which did not contain stabilizing agents possessed a sour smell.

EXAMPLE 2

A base perfume composition for shampoos was prepared by admixing the following ingredients:

| | |
| --- | --- |
| Ethyl-maltol | δ-Undecalactone |
| Linalol | Hexyl acetate |
| Buchu leaf oil | Ethyl acetate |
| α-Methyl-butyric acid | Isobutyl isovalerate |
| Amyl acetate | Benzyl alcohol |

The composition was then divided into several portions and to two of them MONAFAX 785 and MONAFAX L-10 (samples 1 and 2) were separately added at a 5% by weight concentration. To each one of the obtained portions there was added a small amount of iron filings. A few minutes after addition a strong dark-red colour developed in those untreated samples which did not contain the cited stabilizing agents whereas samples 1 and 2 remained perfectly colorless.

By storing the treated and untreated samples in the dark during 8 months, samples 1 and 2 had acquired a pale-yellow colour whereas untreated samples appeared orange-red.

EXAMPLE 3

A perfume composition for deodorizing spray was prepared by admixing the following ingredients:

| | |
| --- | --- |
| Decanol | Epoxy ocimene |
| Methyl-nonylacetaldehyde | Bergamot oil |
| Isobornyl acetate | Linalyl acetate |
| Hexylcinnamic aldehyde | Terpineol |
| Benzyl acetate | Geranium oil |
| Cedar oil | Siberia pine oil |
| Indol | Rosemary oil |
| Methyl dihydrojasmonate | Galbanum oil |
| Neroli bigarade | Lavandin oil |
| Tree moss concrete | Hydroxycitronellal |

The above perfume base composition was used to prepare a novel solution as follows (parts by weight):

| | |
| --- | --- |
| Perfume composition | 1 |
| Bactericide (commercial) | 0.2 |

| -continued | |
|---|---|
| 95% Ethanol | 99 |

To a portion of the thus obtained solution, p-t-butyl-hydroxy-toluene and p-t-butyl-hydroxy anisole were added in a 0.01% and 0.005% by weight concentration respectively (sample 1).

To another portion of the same solution, TETRONIC 1301 was added at a 0.05% by weight concentration (sample 2). By storing an untreated sample of the solution and samples 1 and 2 in the dark for 8 weeks, the untreated sample developed a brown colour, sample 1 presented a slight brown colour whereas sample 2 remained colorless.

EXAMPLE 4

By making use of a base perfume composition similar to that described in Example 3, there was prepared a novel base for deodorizing spray by mixing the following ingredients (parts by weight):

| Perfume composition | 1 |
|---|---|
| Bactericide (commercial) | 0.2 |
| 95% Ethanol | 100 |
| Propellant (FREON 11/12) | 100 |

TETRONIC 1301 was added at a 0.025% concentration to a portion of the obtained solution (sample 1).

To another portion of the same solution there were added TETRONIC in the same concentration (0.025%) and triethanol-amine in an amount sufficient to neutralize the acidity of the medium (sample 2). The obtained samples, as well as a sample of untreated solution, were finally stored 4 weeks at 40° C.

After this period the untreated solution appeared strongly orange-red coloured, sample 1 was pale-yellow, whereas sample 2 remained practically colorless.

A fourth sample (sample 4) was prepared by adding to the solution TETRONIC 1301 (0.025%) and p-t-butyl-hydroxy-toluene (0.01%).

Sample 4 was exposed to sun light during 4 weeks, together with an untreated portion. Sample 4 remained practically colorless and perfectly stable from the point of view of its odour, whereas the untreated solution appeared red-brown and possessed a sour scent.

EXAMPLE 5

By using a base perfume composition (0.5% concentration) similar to that described in Example 3, there was prepared a novel base for dry antiperspirant by mixing the following ingredients
Perfume composition
Aluminum oxychloride
Aluminum allantoinate
Isopropyl myristate
Propellant (FREON 11/12)

To a portion of the above obtained base there was added TETRONIC 1301 at 0.05% concentration.

After storage of the thus stabilized sample together with an untreated sample (4 weeks; 40° C.) it was shown that the stabilized sample possessed the original scent whereas the unstabilized one had lost the original fresh top note.

EXAMPLE 6

A fraction of vetiver oil (Haiti) at 2% in 95% ethanol possessed a sour odour after storage at room temperature during 4 weeks.

By adding to a novel freshly arrived fraction of the same oil 0.1% of TETRONIC 1301 or HOSTAPHAT KL-340 together with a certain amount of triethanol-amine it was possible to completely inhibit the formation of the sour off-odour.

EXAMPLE 7

Methyl 2,4-dihydroxy-3,5-dimethyl-benzoate was used as indicated hereinbelow as perfuming ingredient for the manufacture of toilet soap.

A first sample was obtained by perfuming the soap paste with the mentioned benzoate ester at a concentration of 0.1%. A second sample was prepared by adding to the soap paste, in addition to the benzoate ester, 0.9% of STEINAPHAT EAK 8190. Sample 3 was prepared by adding to the soap paste, in addition to the benzoate ester, 0.9% of STRODEX MO-100. The given concentrations are calculated based on the weight of the total finished product. The added stabilizing ingredients function here also as solvent for the perfume.

A few hours after its manufacture, sample 1 presented already a pale brown colour.

During two-week storage, sample 1 was definitely brown, sample 2 appeared slightly yellow, whereas sample 3 kept its original colour.

EXAMPLE 8

A base perfume composition for toilet soap was constituted by the following ingredients:

| | |
|---|---|
| Decanal | Musk indane |
| Methyl-nonyl acetaldehyde | Epoxy-ocimene |
| Brazil rose wood oil | Petitgrain bigarade |
| Hydroxy-citronellal | Oriental sandel-wood oil |
| Coumarin | Terpineol |
| Hexylcinnamaldehyde | Bergamot oil |
| Ethyl-vanillin | Lime oil |
| Eucalyptol | Isocamphyl-cyclohexanol |
| Geraniol | Synthetic lily-of-the-valley |
| Galbanum oil | Lavandin oil |

The above base was used at 2% to perfume a soap paste. The following samples were prepared and stored for 1 week:

| sample | 1 | 2 | 3 |
|---|---|---|---|
| soap paste | 98.0 | 97.2 | 97.5 |
| perfume base | 2.0 | 2.0 | 2.0 |
| tin chloride | — | 0.8 | — |
| STEINAPHAT EAK 8190 | — | -- | 0.5 |

After one-week storage the colour observed was:

| Sample: |
|---|
| 1: brown |
| 2: beige |
| 3: original colour |

What I claim is:

1. In a method for stabilizing a perfume, perfume base or perfuming ingredient against the adverse effects of the presence of traces of heavy metals including iron and copper, the improvement which consists of adding to said perfume, perfume base or perfuming ingredient, at a weight concentration of from about 0.5 to 25% based on the total weight of the stabilized perfume, perfume base or perfuming ingredient, a liposoluble non-ionic, heavy metal complexing agent selected from (i) a copolymer of ethylene and propylene oxide with ethylene diamine or (ii) an organic ester derived from phosphoric or phosphonic acid and an ethoxylated fatty alcohol.

2. A perfume, perfume base, or perfuming ingredient containing as a stabilizer, a liposoluble non-ionic, heavy metal complexing agent selected from (i) a copolymer of propylene and ethylene oxide with ethylene diamine or (ii) an organic ester derived from phosphoric or phosphonic acid and an ethoxylated fatty alcohol, wherein the complexing agent is present at a weight concentration of from about 0.5 to 25% based on the total weight of the stabilized perfume, perfume base or perfuming ingredient.

3. The perfume, perfume base or perfuming ingredient of claim 2 which contains in addition to the liposoluble heavy metals complexing agent an anti-oxidant and/or an organic base.

4. A method according to claim 1 wherein the complexing agent is an organic ester derived from phosphoric or phosphonic acid and an ethoxylated fatty alcohol.

5. A perfume, perfume base or perfuming ingredient according to claim 2 wherein the complexing agent is a copolymer of ethylene and propylene oxide with ethylene diamine.

* * * * *